(12) United States Patent
Callahan et al.

(10) Patent No.: US 8,609,149 B2
(45) Date of Patent: Dec. 17, 2013

(54) DILUTABLE BIOCIDAL COMPOSITIONS AND METHODS OF USE

(71) Applicant: Stepan Company, Northfield, IL (US)

(72) Inventors: Molly Ryan Callahan, Winnetka, IL (US); Kenneth J. Littel, Hawthorn Woods, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 13/708,503

(22) Filed: Dec. 7, 2012

(65) Prior Publication Data

US 2013/0101677 A1   Apr. 25, 2013

Related U.S. Application Data

(63) Continuation of application No. PCT/US2011/039477, filed on Jun. 7, 2011.

(60) Provisional application No. 61/352,230, filed on Jun. 7, 2010.

(51) Int. Cl.
*A61K 33/40* (2006.01)
*A61K 33/42* (2006.01)
*A61K 33/02* (2006.01)

(52) U.S. Cl.
USPC ............................ 424/616; 424/605; 424/719

(58) Field of Classification Search
USPC ........................................ 424/616, 605, 719
See application file for complete search history.

(56) References Cited

U.S. PATENT DOCUMENTS

| | | | |
|---|---|---|---|
| 3,930,010 A | 12/1975 | Klopping | |
| 2006/0193816 A1* | 8/2006 | Elfersy et al. | ............. 424/70.28 |
| 2007/0059380 A1 | 3/2007 | Ramirez et al. | |
| 2009/0281012 A1* | 11/2009 | Trivedi et al. | ................. 510/138 |
| 2009/0318322 A1 | 12/2009 | Taylor et al. | |

OTHER PUBLICATIONS http://www.google.com/search?q=phosphoric+acid+ph+curve&hl=en&tbm=isch&tbo=u&source=univ&sa=X&ei=c75oUfyWMsvj4AOqx4HQDA&ved=0CC0QsAQ&biw=997&bih=465, live Web, 2013.*
Int'l Search Report for PCT/US11/39477 dated Oct. 19, 2011.

* cited by examiner

*Primary Examiner* — Blessing M Fubara
(74) *Attorney, Agent, or Firm* — McAndrews, Held & Malloy, Ltd.

(57) ABSTRACT

The present technology, in general, relates to antimicrobial and biocidal compositions, for example bucket dilutable biocidal compositions, and the various applications and/or processes of utilizing them as hard surface disinfectants and/or cleaners. The biocidal composition of the present technology comprises hydrogen peroxide, a quaternary ammonium compound, an appropriate acid and an amine oxide in specific concentrations to provide a 5 minute or less microbial contact kill time for at least one biocidal target.

21 Claims, No Drawings

DILUTABLE BIOCIDAL COMPOSITIONS AND METHODS OF USE

RELATED APPLICATIONS

This application is a continuation of International application Serial No. PCT/US2011/039477 (International Publication No. WO 2011/156398), having an International filing date of Jun. 7, 2011. This PCT application claims priority to U.S. provisional patent application Ser. No. 61/352,230, filed Jun. 7, 2010. The entire specifications of the PCT and provisional applications referred to above are hereby incorporated by reference.

FIELD OF THE INVENTION

The present technology, in general, relates to antimicrobial and biocidal compositions, for example bucket dilutable biocidal compositions, and the various applications and/or processes of utilizing them as hard surface disinfectants and/or cleaners.

BACKGROUND OF THE INVENTION

Biocidal compositions, which may be, for example, germicides, antimicrobial or antibacterial blends, are widely used in different industries, hospitals and institutions as well as in consumers' daily lives to inhibit or kill various microorganisms, including bacteria, viruses, fungus, protozoa or other susceptible pathogenic agents (collectively "biocidal targets").

In the United States (US), the Environmental Protection Agency (EPA) tests biocidal compositions using an AOAC (Association of Analytical Chemists) Use Dilution Test (UDT) to determine if a biocidal composition has the disinfectant efficacy claimed. The UDT is a probability based test that determines if a specific contact time, e.g., 5 or 10 minutes, of a test biocidal composition shows no growth for a particular biocidal target, where a pass is at least 59 out of 60 UDT test samples showing no growth. 59 or 60 out of 60 test samples showing no growth ensures a statistical significance of greater than 95% that the test composition will eradicate the bacteria of the inoculum. The criteria for acceptable performance are currently under review at the EPA. A proposed passing criteria being contemplated for the UDT would allow for growth in 3 or less test samples out of 60 to pass. If the proposed changes are accepted, biocidal compositions resulting in no growth in at least 57 or 58 or 59 or 60 out of 60 test samples will successfully demonstrate disinfectant efficacy. Yet another method that is being evaluated at present to possibly replace the UDT in the US at a future date is the OECD Quantitative Test Method for Evaluating Microbiocides on Surfaces which is a quantitative method for evaluating bactericidal activity of microbicides used on hard non-porous surfaces. The proposed criteria for compositions to be able to claim biocidal efficacy is that they need to demonstrate a 4 $\log_{10}$ to a 5 $\log_{10}$ reduction in number of specific target organisms such as *Pseudomonas aeruginosa* (*Pseudomonas*), *Staphylococcus aureus* (*Staphylococcus*), *Salmonella enterica* (*Salmonella*), etc. Alternately efficacy of biocidal compositions is measured by tests such as EN 13697, Quantitative Non-Porous Surface Test for the Evaluation of Bactericidal Activity of Chemical Disinfectants Used in Food, Industrial, Domestic and Institutional Areas in Europe. The European standard is a quantitative method in which an efficacious biocidal composition has to demonstrate a minimum of 4 $\log_{10}$ reduction in number of the target organism.

The industrial standard microbial contact kill time as determined by the EPA-approved Use Dilution test (UDT) for a bucket dilutable composition for major biocidal targets, e.g. *Staphylococcus aureus, Salmonella enterica, Pseudomonas aeruginosa*, etc., is 10 minutes. In other words, for a bucket dilutable disinfectant composition to claim disinfectancy of hard surfaces, the composition must pass the 10 minute contact kill time. There is still a strong need and unforeseeable solution in the art for biocidal compositions that provide shorter contact times (i.e., faster rates of kill, e.g. 5 minutes or less), a broader spectrum of activity, and/or a wider range of applications (e.g., hard surface disinfectants). There is especially a need for more efficacious biocidal products in the disinfectant field to reduce the kill time for problematic biocidal targets in hospital settings, e.g. *Staphylococcus aureus*, and *Pseudomonas aeruginosa*, to provide shorter contact times and thus reduce the likelihood of creating superbugs or bacteria resistant to disinfectants.

BRIEF SUMMARY OF THE INVENTION

The present technology generally relates to biocidal compositions, for example, dilutable biocidal compositions, comprising a quaternary ammonium compound, hydrogen peroxide, amine oxide and a stabilizer; suitably an acidic stabilizer such as, but not limited to, phosphoric acid or glycolic acid or peracetic acid. The compositions of the present technology provide improved biocidal efficacies, for example, a microbial contact kill time of 5 minutes or less. The compositions of the present technology may be used in the industrial, hospital and residential settings.

In one aspect, the present technology provides composition comprising about 7.5% hydrogen peroxide by weight, about 6.4% of a quaternary ammonium compound by weight, about 0.3% amine oxide by weight; about 0.225% phosphoric acid by weight; and water, wherein the quaternary ammonium compound comprises n-alkyl (50% C14, 40% C12, 10% C16) dimethyl benzyl ammonium chloride, n-octyl decyl dimethyl ammonium chloride, di-n-octyl dimethyl ammonium chloride, and di-n-decyl dimethyl ammonium chloride (e.g., BTC® 885 or BTC® 888). In some aspects, the amine oxide is lauramine oxide. In other aspects, the composition is a dilutable composition diluted in a diluent at a ratio of 1:10, 1:32, or 1:64.

In another aspect, the present technology provides a dilutable biocidal composition comprising about 7% to about 7.5% by weight hydrogen peroxide; about 6% to about 6.8% by weight quaternary ammonium compound; about 0.25% to about 0.35% by weight amine oxide; about 0.2% to about 0.4% by weight acidic stabilizers, such as phosphoric acid; and water, wherein the dilutable biocidal composition, when diluted, provides a microbial contact kill time of less than about 5 minutes for at least one biocidal target, and wherein the quaternary ammonium compound comprises n-alkyl (50% C14, 40% C12, 10% C16) dimethyl benzyl ammonium chloride, n-octyl decyl dimethyl ammonium chloride, di-n-octyl dimethyl ammonium chloride, and di-n-decyl dimethyl ammonium chloride (e.g., BTC® 885 or BTC® 888).

In yet another aspect the present technology provides a dilutable biocidal composition comprising about 7.4% to about 7.6% by weight hydrogen peroxide; about 6.2% to about 6.6% by weight quaternary ammonium compound; about 0.28% to about 0.32% by weight amine oxide; and about 0.22% to about 0.24% by weight acid stabilizers, such as phosphoric acid. In yet a further aspect, the dilutable biocidal composition comprises about 7.5% by weight hydrogen peroxide, about 6.4% by weight quaternary ammonium compound, about 0.3% by weight amine oxide, and about 0.225% by weight phosphoric acid.

In yet another aspect, the present technology provides method of cleaning a hard surface comprising providing a composition comprising about 1172 ppm hydrogen peroxide, about 1000 ppm quaternary ammonium compound, about 47 ppm amine oxide, about 35 ppm phosphoric acid, and water. The method further includes contacting at least one soiled surface or substrate with the composition; and removing the composition or soil from the surface or substrate.

In yet a further aspect, the present technology provides a method of disinfecting a hard surface from at least one biocidal target including providing a composition comprising about 1172 ppm hydrogen peroxide, about 1000 ppm quaternary ammonium compound, about 47 ppm amine oxide, about 35 ppm phosphoric acid, and water. The method further includes contacting the hard surface with the composition for 5 minutes or less.

In yet another aspect, the present technology provides a method of destroying, inhibiting or eliminating the growth of at least one biocidal target comprising the steps of providing at least one dilutable biocidal composition comprising about 1172 ppm hydrogen peroxide, about 1000 ppm quaternary ammonium compound, about 47 ppm amine oxide, about 35 ppm phosphoric acid, and water to at least one surface or substrate for a sufficient contact time to destroy, inhibit or eliminate growth of the at least one microbial target.

DETAILED DESCRIPTION OF THE INVENTION

While the presently described technology will be described in connection with one or more preferred embodiments, it will be understood by those skilled in the art that the technology is not limited to only those particular embodiments. To the contrary, the presently described technology includes all alternatives, modifications, and equivalents that can be included within the spirit and scope of the appended claims.

As used herein, the term "biocidal" means capable of destroying, killing, neutralizing, reducing, eliminating, or inhibiting the growth of bacteria, microorganisms, germs, viruses, spores, molds, yeasts, algae, and/or other susceptible pathogenic agents; biocidal can be, for example, antimicrobial, antibacterial, germicidal, sporicidal, antiviral, disinfectant, etc.

A "ready-to-use" or "RTU" product, composition or formulation of the present technology refers to a product, composition, or formulation that is ready to be applied to articles or surfaces to be biocidally treated and/or disinfected.

A "dilutable," "concentrate," or "dilutable concentrate" product, composition, or formulation of the present technology refers to a product, composition, or formulation that needs to be diluted with a diluent (e.g., water) in a ratio of, for example, 1:64, 1:32, 1:16, or 1:10, among others, before it can be applied to articles, substrates, or surfaces to be biocidally treated or disinfected.

As used herein, a "diluent" or "carrier" means a liquid or solid substance, or mixture of substances, that can be used as a delivery vehicle or carrier to prepare or dilute at least one biocidal composition of the present technology. A diluent can be, for example, water.

"Biocidal targets" are organisms targeted to be inhibited or killed by a biocidal agent. These organisms include microorganisms including, for example, algae, gram negative and gram positive bacteria, enveloped and non-enveloped viruses, and fungi, including molds and yeasts.

The EPA-approved and industrial standard for a claimed microbial contact kill time efficacy for a bucket dilutable composition for major biocidal targets, e.g. *Staphylococcus aureus, Salmonella enterica, Pseudomonas aeruginosa*, etc., is 10 minutes. In actual use in industrial and hospital settings, there is a need for shorter contact times to approximate use in the real world settings where the practicality of a disinfectant contacting a work surface for 10 minutes or more is only under ideal circumstances and any reduction in the contact time would allow for approximating working conditions.

Unexpectedly, the present technology provides a biocidal composition that provides a microbial contact kill time of 5 minutes or less for the major biocidal targets, e.g. *Staphylococcus aureus, Salmonella enterica*, and *Pseudomonas aeruginosa*. The present technology provides a biocidal composition comprising hydrogen peroxide, a quaternary ammonium compound BTC® 885 or BTC®888, an amine oxide, and an acidic stabilizer which provides a microbial kill time of 5 minutes or less for at least one biocidal target. The composition is balanced to the desired amounts by water. Not to be bound by any particular theory, it is believed that the specific combination of these components provides a synergistic effect that increases the biocidal efficacy. Any of the components alone or if one of the components is missing from the combination, does not provide the desired 5 minute microbial contact kill time of the present technology.

The biocidal composition of the present technology includes about 6% to about 6.8%, alternatively between about 6.2% to about 6.6%, preferably from about 6.4% to about 6.5% of a quaternary ammonium compound, BTC® 885 or BTC® 888, provided by Stepan Company, Northfield, Ill. BTC® 885 comprises n-alkyl dimethyl benzyl ammonium chloride and dialkyl dimethyl ammonium chloride (mixture of n-Alkyl (50% C14, 40% C12, 10% C16) dimethyl benzyl ammonium chloride, n-octyl decyl dimethyl ammonium chloride, di-n-octyl dimethyl ammonium chloride, and di-n-decyl dimethyl ammonium chloride) provided by Stepan Company, Northfield, Ill. BTC® 888 comprises n-alkyl dimethyl benzyl ammonium chloride and dialkyl dimethyl ammonium chloride (mixture of n-alkyl dimethyl benzyl ammonium chloride mixture of n-Alkyl dimethyl benzyl ammonium chloride, n-octyl decyl dimethyl ammonium chloride, di-n-octyl dimethyl ammonium chloride, and di-n-decyl dimethyl ammonium chloride) provided by Stepan Company, Northfield, Ill. For example, the quaternary ammonium compound may comprise about 6%, about 6.1%, about 6.2%, about 6.3%, about 6.4%, about 6.5%, including additional increments of, for example, 0.01%, 0.02%, 0.05%, 0.1%, 0.15%, or 0.2% and multiple factors thereof (e.g. ×1, ×2, ×3, ×4, etc). Surprisingly and unexpectedly, as demonstrated in the examples below, other quaternary ammonium compounds do not provide the desired biocidal efficacy in the practice of the biocidal compositions of the present technology. It is the specific combination of BTC 885® or BTC®888 quaternary ammonium compounds, hydrogen peroxide, amine oxide and the acidic stabilizer that provides the desired biocidal efficacy in the amounts disclosed in the present technology.

The biocidal composition of the present technology includes hydrogen peroxide at about 7.0% to about 7.5% by weight of the composition, more preferably about 7.3% to about 7.5%, most preferably at about 7.5%, for example, about 7.1%, about 7.2%, about 7.3%, about 7.4%, about 7.5%, including additional increments of, for example, 0.01%, 0.02%, 0.05%, 0.1%, 0.15%, or 0.2% and multiple factors thereof (e.g. ×1, ×2, ×3, ×4, etc). For hydrogen peroxide to be effective, a substantial proportion of the hydrogen peroxide must survive on the shelf until use. Hydrogen peroxide slowly decomposes spontaneously, which can be accelerated by catalytically active substances, such as metal ions. Thus, a stabilizer is provided in the biocidal compositions to stabilize the hydrogen peroxide in solution with the other active ingredients. Hydrogen peroxide is desired to be kept under 8% which is a safe level for shipment and storage without triggering hazardous material warnings. Hydrogen peroxide alone at these concentrations does not have a microbial kill time of 5 minutes or less.

The biocidal compositions of the present technology include a stabilizer that helps to stabilize the hydrogen peroxide from decomposing during storage, suitably an acidic stabilizer. A preferred stabilizer includes, but is not limited to, phosphoric acid or glycolic acid or peracetic acid. The stabilizer comprises about 0.2% to about 0.4% by weight of the biocidal composition, alternatively about 0.22% to about 0.3%, preferably about 0.225% by weight of the biocidal composition, for example, about 0.22%, about 0.23%, about 0.235%, about 0.24%, about 0.25%, about 0.26%, about 0.27%, about 0.28%, including additional increments of, for example, 0.01%, 0.02%, 0.05%, 0.1%, 0.15%, or 0.2% and multiple factors thereof (e.g. ×1, ×2, ×3, ×4, etc). Other suitable acids are contemplated to be used as stabilizers in the compositions of the present technology.

Stability of biocidal compositions is important for commercial use of such products to ensure biocidal efficacy does not diminish over time. Hydrogen peroxide is known to be unstable over time, and thus it was surprisingly found that the stabilizer used, for example, phosphoric acid, in combination with hydrogen peroxide and BTC 885® provides a stable concentrate. Not to be bound by any particular theory, the biocidal compositions of the present invention are believed to be stable, both thermally and over time. Stability is desired for the biocidal composition to retain its useful properties on the timescale of its expected usefulness. The compositions of the present technology can be stable at temperatures of from about 4° C. to about 50° C., alternatively about 25° C. to about 40° C. In some embodiments, the compositions are stable at about 25° C. for at least about 2 weeks, alternatively at least about 4 weeks, alternatively at least about 6 weeks. The compositions can have a shelf life and can be stable at about 25° C. for at least about 1 day, at least about 3 days, at least about 1 week, at least about 2 weeks, at least about 3 weeks, at least about 4 weeks, at least about 5 weeks, at least about 6 weeks, at least about 7 weeks, at least about 8 weeks, at least about 10 weeks, at least about 12 weeks, at least about 15 weeks, at least about 18 weeks, at least about 20 weeks, at least about 24 weeks, at least about 26 weeks, at least about 28 weeks, at least about 30 weeks, at least about 32 weeks, at least about 34 weeks, at least about 36 weeks, at least about 38 weeks, at least about 40 weeks, at least about 50 weeks, or at least 52 weeks. The biocidal compositions of the present technology preferably are stable at room temperature (about 25° C.) for at least one year. Surprisingly, the biocidal compositions of the present technology were found to be stable at about 40° C. to about 50° C. for at least a month. In some embodiments, the biocidal compositions of the present technology can be stable at about 40° C. to about 50° C. for at least about 2 weeks, at least about 4 weeks, at least about 6 weeks, at least about 10 weeks, at least about 12 weeks, at least about 14 weeks, at least about 15 weeks, at least about 20 weeks, at least about 24 weeks, at least about 30 weeks, at least about 34 weeks, or at least about 40 weeks.

The biocidal composition of the present technology further comprises at least one amine oxide. One suitable amine oxide is AMMONYX® LO (lauramine oxide) available from Stepan Company, Northfield, Ill. The present biocidal compositions comprise the amine oxide at about 0.25% to about 0.35% by weight of the biocidal composition, alternatively about 0.28% to about 0.32%, preferably about 0.3% by weight of the biocidal composition, for example, about 0.26%, about 0.27%, about 0.28%, about 0.29%, about 0.3%, about 0.31%, about 0.32%, about 0.33%, including additional increments of, for example, 0.01%, 0.02%, 0.05%, 0.1%, 0.15%, or 0.2% and multiple factors thereof (e.g. ×1, ×2, ×3, ×4, etc). Other suitable amine oxides are contemplated to be used in the present technology, and include, but are not limited to, octyl amine oxides, decyl amine oxides, stearamine oxides, cetamide oxides, myristamine oxides, lauramidoproplyamine oxides and tetradecyl amine oxides, for example, but not limited to, AMMONYX® CO (cetamide oxide), AMMONYX® DO (decyl amine oxide), AMMONYX® MO (myristamine oxide), AMMONYX® SO (steramine oxide) and AMMONYX® LMDO (lauramidopropylamine oxide), available from Stepan Company, Northfield, Ill.

In some embodiments, the biocidal composition is a dilutable biocidal composition which is diluted by a suitable diluent. Preferably, in some embodiments, the diluent is water. Suitable water to dilute the compositions of the present technology includes, but is not limited to, hard water, soft water, distilled water, de-ionized water or combinations thereof. The compositions of the present technology are preferably diluted with ambient, e.g., room temperature (about 25° C.) water, but may be used with water at other temperatures, for example, temperatures above 25° C.

In accordance with another embodiment of the present technology, the biocidal composition can be a dilutable concentrate product. As defined above, a dilutable concentrate product is a product that requires dilution with a diluent (e.g., water) in a ratio of about, for example, 1:64, 1:32, 1:16 or 1:10 among others, before it can be applied to articles or surfaces to be biocidally treated or disinfected. In a preferred embodiment of the present technology, the biocidal composition is a dilutable composition that is diluted with water at a ratio of 1:64.

Dilutable biocidal compositions in some embodiments are preferred as a cost saving and money saving option which reduces packaging and shipping cost and may be diluted to the working concentration on site. In other embodiments, the dilutable concentrate may be diluted, for example, 1:10, 1:16, 1:32, or preferably 1:64 and packaged as a ready to use liquid or spray. For example, an end use concentration of a 1:64 dilution of the biocidal composition of the present invention includes about 1172 ppm hydrogen peroxide, about 1000 ppm BTC® 885 (or BTC® 888), about 47 ppm amine oxide (for example AMMONYX® LO), and about 35 ppm phosphoric acid, balanced with water.

In some embodiments, the end use concentration of a biocidal composition comprises about 1000 ppm to about 1200 ppm hydrogen peroxide, about 900 ppm to about 1100 ppm BTC® 885 or BTC® 888, about 30 ppm to about 50 ppm amine oxide, and about 25 ppm to about 45 ppm phosphoric acid balanced with water.

The biocidal compositions of the present technology are capable of inhibiting, reducing or eliminating growth of a wide range of biocidal targets. The biocidal targets can include, but are not limited to: green algae such as *Chlorella vulgaris, Scenedesmus obliquus, Ulothrix lactuca*, blue-green algae such as *Oscillatoria lutea, Phormidium inundatum, Anabaena verrucosa*, gram negative bacteria such as *Campylobacter jejuni, Pseudomonas aeruginosa, Salmonella enterica*, gram positive bacteria such as *Staphylococcus*

*aureus, Streptococcus pyogenes, Clostridium difficile*, enveloped viruses such as Avian Influenza Virus, Hepatitis B Virus, West Nile Virus, Human Immunodeficiency Virus (HIV), non-enveloped viruses such as Adenovirus, Feline calicivirus, Hepatitis A Virus, Polio Virus, molds such as *Penicillium mameffei, Aspergillus niger, Trichophyton mentographytes*, and yeasts such as *Candida albicans, Saccharomyces cerevisiae, Cryptococcus albidus*. Although this listing of biocidal targets is not intended to be exhaustive, it will be appreciated by those skilled in the art that the biocidal compositions of the present technology exhibit an enhanced efficacy. Use of the biocidal compositions and methods of the present technology to inhibit, reduce or eliminate the growth of microbiological spores and vegetative cells, for example, *Clostridium Difficile*, is also contemplated. Use of biocidal compositions and methods of the present technology to inhibit, reduce, or eliminate growth of protozoa, dust mites, parasites, biofilms, worms and helminthic organisms is also contemplated.

Thus, the biocidal compositions of the present technology can have a microbial contact kill time of less than about 10 minutes, preferably a microbial contact kill time of less than 5 minutes, alternatively about 4 minutes or less, alternatively about 3 minutes or less, alternatively about 2 minutes or less, alternatively about 1 minute or less, or alternatively about 30 seconds or less for at least one biocidal target. For some particular embodiments with bactericidal properties, the microbial contact time for at least one bacteria is suitably about 5 minutes or less, for example, about 5 minutes, about 4 minutes, about 3 minutes, about 2 minutes, about 1 minute, or about 30 seconds. For other embodiments of biocidal compositions with virocidal properties, the microbial contact time for at least one virus is suitably about 5 minutes or less, for example, about 5 minutes, about 4 minutes, about 3 minutes, about 2 minutes, about 1 minute, or about 30 seconds. In some embodiments, the biocidal composition may have sporicidal properties and have a microbial contact kill time of 10 minutes or less, alternatively 5 minutes or less.

In some embodiments, the biocidal composition is a dilutable biocidal composition and is tested by diluting the biocidal composition at the proper diluent ratio under hard water conditions and with an organic soil load. "Hard water conditions" include water with high mineral content, e.g., at least about 200 ppm, more preferably about 400 ppm calcium or magnesium ions. Under testing conditions, synthetic hard water can be provided by adding 200 ppm or 400 ppm $CaCO_3$ in the mixture. An organic soil load is provided to mimic dirt associated with a dirty surface to be cleaned, and in testing conditions well known in the art, for example, can be bovine serum albumin (BSA), horse serum, etc. Suitable organic loads for testing are about 5% of the biocidal target solution.

Unexpectedly, the ability of the biocidal composition to provide an enhanced biocidal efficacy does not necessarily correlate with increased amounts of ingredients in the composition. Rather, it is believed that a combination of the specific concentrations of the quaternary ammonium compound BTC® 885 or BTC®888, the hydrogen peroxide, the amine oxide and the acidic stabilizer disclosed in the present technology result in biocidal compositions which provide an unexpected synergistic biocidal efficacy, e.g., a shorter microbial contact time of about 5 minutes or less for at least one biocidal target. As demonstrated in the examples below, more or less of one or more of these components in the composition results in failure to pass the Use Dilution Test. Thus, it is completely unpredictable what concentrations of the components would provide this unexpected 5 minute or less microbial contact kill time. For example, other amounts of quaternary ammonium compound BTC® 885 or BTC®888, such as, for example, 5.75% or 7.0%, do not provide a microbial contact kill time of 5 minutes. Further, substituting other quaternary ammonium compounds, for example the same amount of other quaternary ammonium compound, e.g., BTC® 1210 quaternary ammonium compound, available from Stepan Company, Northfield, Ill., for the BTC® 885 quaternary ammonium compound, even at identical amounts, does not provide a microbial contact kill time of 5 minutes. Thus, it is completely unpredictable what specific combination of components and, in what concentrations, will provide a 5 minute or less microbial contact kill time.

The biocidal compositions of the present technology also surprisingly provide biocidal efficacy without employing EDTA or high concentrations of solvent to act as potentiators in the compositions. Quaternary ammonium compounds alone do not act quickly enough to provide even a 10 minute microbial contact kill time, and therefore require the addition of a potentiator in order to improve the efficacy of the quaternary ammonium compound. Typical potentiators, such as EDTA and solvents, for example, diethylene glycol monobutyl ether, exhibit certain drawbacks. For example, EDTA is not an environmentally friendly component, and diethylene glycol monobutyl ether or other solvents can be incompatible with the surfaces to be disinfected. Desirably, and unexpectedly, the biocidal compositions of the present technology can achieve a 5 minute microbial contact kill time without utilizing either EDTA or solvents as a potentiator.

Standard blending equipment is acceptable for preparing the biocidal compositions of the present technology. Preparation, handling, and packaging precautions employed can be consistent with those established for quat-based formulations known in the art.

The biocidal compositions of the present technology can have a specific pH range for optimal use at the end use concentration of the dilutable, depending on the particular end use and type of surface treated. The biocidal composition described herein can have an end use concentration pH between about 6 and about 8. One suitable composition has a pH between about 6.5 and about 7.5. For example, the pH of the biocidal composition can be about 6.0, about 6.2, about 6.3, about 6.4, about 6.5, about 6.6, about 6.7, about 6.8, a about 6.9, about 7.0, about 7.1, about 7.2, about 7.3, about 7.4, about 7.5, about 7.6, about 7.7, about 7.8, about 7.9, or about 8.0.

In some embodiments, the biocidal composition may be used in a concentrated form. The pH of a concentrated biocidal composition can be, for example, a pH of about 5 or less, preferably a pH of about 4 or less.

The biocidal compositions of the present technology have a critical micelle concentration (CMC) at their end use concentration of between about 300 ppm to about 450 ppm of the quat, preferably from about 350 ppm to about 400 ppm, for example, about 373 ppm, and include additional increments therebetween, for example, about 1 ppm, about 2 ppm, about 5 ppm, about 10 ppm, about 20 ppm, about 25 ppm, about 30 ppm and multiple factors thereof (e.g. ×1, ×2, ×3, ×4, etc). Not to be bound by any particular theory, it is believed that the preferred quaternary ammonium compound (BTC 885®) has shorter hydrophobic tail lengths allowing for closer packing of the molecules and thus providing the proper balance of surface tension and micelles to enhance the biocidal efficiency of the composition. Any known tensiometer known in the art may be used for calculating the critical micelle concentration, including, but not limited to, for example, Sigma 700/701, provided by Attension, a part of BiolinScientific, Linthicum, Md., or DU Nouy tensiometer (kruss type 8451).

In some embodiments of the present application, the biocidal composition is envisioned to be used as a spray. The biocidal composition may be used as a spray in its undiluted formulation, or used as a ready to use spray using a 1:10, 1:32 or preferably a 1:64 dilution of the biocidal composition. In some embodiments, the composition may be used in a wipe, such as a wipe used with an applicator pad, for example, SWIFFER® wet disposable cloths, available from Procter and Gamble, Cincinnati, Ohio.

In some embodiments, the present application provides a method of cleaning a hard surface by providing a biocidal composition of the present technology at its end use concentration and contacting at least one soiled surface or substrate with the composition for a set period of time and then removing the composition or soil from the surface or substrate.

Further, in other embodiments, the present application provides a method of disinfecting a hard surface by providing a biocidal composition of the present technology at its end use concentration and contacting the at least one surface to be disinfected with the composition. In some embodiments, the surface to be disinfected is contacted for a specific amount of time, for example, preferably for about 5 minutes or less, alternatively for about 3 minutes or less, and then the composition is removed from the surface.

The methods of contacting a surface with the biocidal composition to clean and/or disinfect a hard surface are contemplated to be used with, for example, but not limited to, a mop, a sponge, a rag, a towel, an automatic floor cleaning device, a manual floor cleaning device, a wet pad applicator, and the like, for example a Swiffer® WetJet or SWIFFER® Wet Disposable cloths to be used with the applicator pads.

In some embodiments the use of the biocidal composition for cleaning and/or disinfecting of a hard surface does not leave streaking or a film on the surface being treated.

Suitable methods of determining an increase in biocidal efficacy are known in the art. Biocidal efficacy can be measured as an increase in percentage kill for a biocidal target after a specified time in contact with the composition (e.g. efficacy percentage). The EPA has regulations regarding required contact times for different surfaces and also accepted regulatory protocols for testing, which are known to one skilled in the art.

In another embodiment, the increased biocidal efficacy can be measured as a decrease in the kill time of a composition, e.g. the amount of time necessary to kill at least 99.9% of the biocidal target on a surface after a specified contact time. The EPA-approved and industrial standard contact time for a bucket dilutable composition using a use dilution test for major biocidal targets, e.g. *Staphylococcus aureus, Salmonella enterica*, and *Pseudomonas aeruginosa*, etc., is 10 minutes. Dilutable biocidal compositions of the present technology can have a kill time of at least about 5 minutes or less, alternatively at least about 4 minutes or less, alternatively at least about 3 minutes or less, alternatively at least about 2 minutes or less.

Any of the embodiments of biocidal compositions described herein can be used as a hospital disinfectant. In suitable embodiments, the hospital disinfectant has a microbial contact kill time for *Staphylococcus aureus* of approximately 5 minutes or less. In other suitable embodiments, the hospital disinfectant has a microbial contact kill time for *Salmonella enterica* of approximately 5 minutes or less. In still other embodiments, the biocidal composition has a microbial contact kill time for *Pseudomonas aeruginosa* of approximately 5 minutes or less. In a particularly suitable embodiment, the biocidal compositions have an approximately 5 minute or less microbial contact kill time for *Staphylococcus aureus, Salmonella enterica*, and *Pseudomonas aeruginosa*.

The term "hard surfaces" as used herein, for example and in some cases preferably, include hard surfaces typically found associated with medical facilities, for example, hospitals, clinics, nursing homes, extended care facilities as well as laboratories among other industrial and/or commercial settings. Further, in some embodiments, the hard surfaces may be associated with residential settings, for example, residential dwellings, meeting halls, schools, recreational facilities and the like.

Further, the term "hard surfaces" includes hard-surfaces typically found in and around residential dwellings like bathrooms, kitchens, basements and garages, for example, floors, walls, tiles, windows, sinks, showers, shower plasticized curtains, wash basins, drains, dishes, fixtures, and fittings and the like made of different materials like fiberglass and other car materials, leather, ceramic, painted and un-painted wood or concrete (for example, as a graffiti remover), varnished or sealed, plaster, bricks, vinyl, no-wax vinyl, linoleum, marble, melamine, FORMICA® (commercially available from Formica Corporation, located in Cincinnati, Ohio), CORIAN® (commercially available from DuPont, located in Wilmington, Del.), glass, any plastics, metals, chromed surfaces and the like. "Hard surfaces" also includes household appliances including, but not limited to, washing machines, automatic dryers, refrigerators, freezers, ovens, microwave ovens, dishwashers, etc. In a preferred embodiment, the surfaces set forth herein are hard surfaces composed of refractory materials such as: glazed and unglazed tile, porcelain, ceramics as well as stone, including marble, granite, and other stone surfaces; glass; metals, for example, stainless steel or aluminum; plastics, for example, polyester, vinyl; fiberglass, FORMICA® (commercially available from Formica Corporation, located in Cincinnati, Ohio), CORIAN® (commercially available from DuPont, located in Wilmington, Del.) and other hard surfaces known to the industry. Even more preferably, the hard surfaces herein are lavatory fixtures such as shower stalls, bathtubs and bathing appliances (racks, shower doors, shower bars) toilets, bidets, wall and flooring surfaces especially those which include refractory materials, among others. Even more preferably, the hard surfaces herein are those associated with kitchen environments and other environments associated with food preparation, including cabinets and countertop surfaces, as well as walls and floor surfaces, especially those which include refractory materials, plastics, FORMICA® (commercially available from Formica Corporation, located in Cincinnati, Ohio), CORIAN® (commercially available from DuPont, located in Wilmington, Del.) and stone. Hard surface cleaning products of the present technology can be made at a neutral pH, but often are made into formulations that exhibit an acid or alkaline pH to get improved cleaning. The stains and soils that are removed from hard surfaces can be organic or inorganic in nature. The type of soils that are to be removed may dictate the preferred pH of the resultant cleaning formula desired. When used as a neutral cleaner, the biocidal composition should have a pH of about 6.0 to about 8.0. A neutral pH is preferred for safety of the user and for hard surface materials which can be adversely affected by high alkaline or acidic cleaners.

The composition of the present technology can be evaluated for cleaning ability by methods described in ASTM D4488-95, "Standard Guide for Testing Cleaning Performance of Products Intended fro Use on Resilient Flooring and Washable Walls", ASTM International, 2001, p. 1-15, incorporated by reference in its entirety, for % soil removal to determine the cleaning effectiveness of the formulations, for example Section 5. Other suitable methods of testing cleaning efficacy known to one skilled in the art can also be used. The compositions of the present technology may also be tested by a filming and streaking method to determine if they film or streak a hard surface.

It should be noted that, as used in the specification and the appended claims, the singular form "a", "an," and "the" include plural references unless the context clearly dictates otherwise.

The presently described technologies and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appended to this specification, and any alterations, modifications, or equivalents of those claims.

EXAMPLES

The compositions and processes described here, and ways to use them are illustrated by the following examples.

Example 1

Use-Dilution Method for Determining Antimicrobial Efficacy

Biocidal efficacy of exemplary dilutable concentrate formulations (control, conventional comparative, or of the present technology) used in the examples are evaluated against *Staphylococcus aureus* and/or *Pseudomonas aeruginosa*. The testing was performed in accordance with the protocols outlined in Chapter 6 of "Official Methods of Analysis" of the Association of Official Analytical Chemists (AOAC) (17th Ed. 1998). More specifically, the protocols involved are AOAC Official Method 955.14 Testing Disinfectants against *Staphylococcus aureus* (§6.2.04) and AOAC 964.02 Testing Disinfectants against *Pseudomonas aeruginosa* (§6.02.06). The contents of Methods 955.14 and 964.02 and the methods referred therein (Methods 955.12, 955.14, and 955.14C) are all incorporated herein by reference in their entirety. The testing method is commonly referred to as the AOAC Use-Dilution Method.

The dilutable concentrates are tested in the presence of 400 parts per million (ppm) (as $CaCO_3$) synthetic hard water and 5% organic soil load.

The efficacy of a biocidal composition according to the Use-Dilution Method can be indicated by the ratio of the number of tested carriers that show growth of the organisms on them over the total number of tested carriers bearing the test organisms that are treated with the test biocidal composition for a pre-selected contact time. For example, a result of "0/60" indicates that the test organisms show growth on zero (0) of the 60 carriers bearing the test organisms that are treated with the tested biocidal composition for the pre-selected contact time (e.g., 10 or 5 minutes). The "0/60" result shows that the growth of the microorganisms has been 100% inhibited. On the other hand, a "2/60" result shows that the organisms grow on two (2) of the 60 tested carriers and the growth inhibition rate is only 96.67%. In the examples, the standard for efficacy of biocidal compositions used are as follows:
Pass EPA efficacy claims: 0/60 or 1/60
Fail EPA efficacy claims: ≥2/60.

These pass/fail rates are based on the current EPA standards. These pass/fail rates may change due to changes in EPA standards. If the EPA revises their standards, this may alter the formulations that are contemplated with the present technology.

Example 2

Antimicrobial Efficacy

The formulation of the present technology, Test Formulation 1, was tested using the Use Dilution Test with a microbial contact kill time of 5 minutes in comparison to a prior art formulation and other formulations with greater than or less than amounts of each specific component at a 1:64 dilution (see Tables 1-18). The components of the tested formulations can be found below. The results of the Use Dilution Test Method can be found in Table 19. Only the formulations of the present technology, Formulations 1, 3 and 4 passed the current UDT with a 5 minute microbial contact kill time.

TABLE 1

| Formulation Number | Component | % active in Concentrate | 1:64 Dilution |
|---|---|---|---|
| 1 (3480-47) | Hydrogen Peroxide | 7.5% | 1172 ppm |
| | BTC 885 | 6.4% | 1000 ppm |
| | AMMONYX LO | 0.3% | 47 ppm |
| | Phosphoric Acid | 0.225% | 35 ppm |

TABLE 2

| Formulation Number | Component | % active in Concentrate | 1:64 Dilution |
|---|---|---|---|
| 2 (prior art) | Hydrogen Peroxide | 7.5% | 1172 ppm |
| | BTC 885 | 5.75% | 900 ppm |
| | AMMONYX LO | 0.3% | 47 ppm |
| | Phosphoric Acid | 0.225% | 35 ppm |

TABLE 3

| Formulation Number | Component | % active in Concentrate | 1:64 Dilution |
|---|---|---|---|
| 3 (3509-02) | Hydrogen Peroxide | 7.5% | 1172 ppm |
| | BTC 885 | 6.4% | 1000 ppm |
| | AMMONYX LO | 0.3% | 47 ppm |
| | Phosphoric Acid | 0.225% | 35 ppm |

TABLE 4

| Formulation Number | Component | % active in Concentrate | 1:64 Dilution |
|---|---|---|---|
| 4 (3509-01) | Hydrogen Peroxide | 7.5% | 1172 ppm |
| | BTC 885 | 6.4% | 1000 ppm |
| | AMMONYX LO | 0.3% | 47 ppm |
| | Phosphoric Acid | 0.225% | 35 ppm |

TABLE 5

| Formulation Number | Component | % active in Concentrate | 1:64 Dilution |
|---|---|---|---|
| 5 (3491-100) | Hydrogen Peroxide | 7.5% | 1172 ppm |
| | BTC 885 | 6.4% | 1000 ppm |

TABLE 5-continued

| Formulation Number | Component | % active in Concentrate | 1:64 Dilution |
|---|---|---|---|
| | AMMONYX LO | 0.225% | 35 ppm |
| | Phosphoric Acid | 0.225% | 35 ppm |

TABLE 6

| Formulation Number | Component | % active in Concentrate | 1:64 Dilution |
|---|---|---|---|
| 6 (3509-77) | Hydrogen Peroxide | 7.5% | 1172 ppm |
| | BTC 885 | 6.4% | 1000 ppm |
| | AMMONYX LO | 0.0% | 0 ppm |
| | Phosphoric Acid | 0.225% | 35 ppm |

TABLE 7

| Formulation Number | Component | % active in Concentrate | 1:64 Dilution |
|---|---|---|---|
| 7 (3491-19) | Hydrogen Peroxide | 7.5% | 1172 ppm |
| | BTC 1210 | 6.4% | 1000 ppm |
| | AMMONYX LO | 0.3% | 47 ppm |
| | Phosphoric Acid | 0.225% | 35 ppm |

TABLE 8

| Formulation Number | Component | % active in Concentrate | 1:64 Dilution |
|---|---|---|---|
| 8 (3480-88) | Hydrogen Peroxide | 7.5% | 1172 ppm |
| | BTC 885 | 7.0% | 1100 ppm |
| | AMMONYX LO | 0.3% | 47 ppm |
| | Phosphoric Acid | 0.225% | 35 ppm |

TABLE 9

| Formulation Number | Component | % active in Concentrate | 1:64 Dilution |
|---|---|---|---|
| 9 (3491-93) | Hydrogen Peroxide | 7.5% | 1172 ppm |
| | BTC 885 | 8.0% | 1250 ppm |
| | AMMONYX LO | 0.3% | 47 ppm |
| | Phosphoric Acid | 0.225% | 35 ppm |

TABLE 10

| Formulation Number | Component | % active in Concentrate | 1:64 Dilution |
|---|---|---|---|
| 10 (3533-24) | Hydrogen Peroxide | 7.5% | 1172 ppm |
| | BTC 885 | 6.4% | 1000 ppm |
| | AMMONYX LO | 0.6% | 94 ppm |
| | Phosphoric Acid | 0.225% | 35 ppm |

TABLE 11

| Formulation Number | Component | % active in Concentrate | 1:64 Dilution |
|---|---|---|---|
| 11 (3491-29) | Hydrogen Peroxide | 7.5% | 1172 ppm |

TABLE 11-continued

| Formulation Number | Component | % active in Concentrate | 1:64 Dilution |
|---|---|---|---|
| | BTC 885 | 6.4% | 1000 ppm |
| | AMMONYX LO | 0.9% | 141 ppm |
| | Phosphoric Acid | 0.225% | 35 ppm |

TABLE 12

| Formulation Number | Component | % active in Concentrate | 1:64 Dilution |
|---|---|---|---|
| 12 (3491-06) | Hydrogen Peroxide | 7.5% | 1172 ppm |
| | BTC 1210 | 8.0% | 1250 ppm |
| | AMMONYX LO | 0.9% | 141 ppm |
| | Phosphoric Acid | 0.225% | 35 ppm |

TABLE 13

| Formulation Number | Component | % active in Concentrate | 1:64 Dilution |
|---|---|---|---|
| 13 (3491-68) | Hydrogen Peroxide | 7.5% | 1172 ppm |
| | BTC 2125M | 6.4% | 1000 ppm |
| | AMMONYX LO | 0.3% | 47 ppm |
| | Phosphoric Acid | 0.225% | 35 ppm |

TABLE 14

| Formulation Number | Component | % active in Concentrate | 1:64 Dilution |
|---|---|---|---|
| 14 (3591-56) | Hydrogen Peroxide | 7.5% | 1172 ppm |
| | BTC 2125M | 6.4% | 1000 ppm |
| | AMMONYX LO | 0.9% | 141 ppm |
| | Phosphoric Acid | 0.225% | 35 ppm |

TABLE 15

| Formulation Number | Component | % active in Concentrate | 1:64 Dilution |
|---|---|---|---|
| 15 (3491-91) | Hydrogen Peroxide | 7.8% | 1218 ppm |
| | BTC 885 | 6.4% | 1000 ppm |
| | AMMONYX LO | 0.3% | 47 ppm |
| | Phosphoric Acid | 0.225% | 35 ppm |

TABLE 16

| Formulation Number | Component | % active in Concentrate | 1:64 Dilution |
|---|---|---|---|
| 16 (3509-48) | Hydrogen Peroxide | 0% | 0 ppm |
| | BTC 885 | 6.4% | 1000 ppm |
| | AMMONYX LO | 0.3% | 47 ppm |
| | Phosphoric Acid | 0.225% | 35 ppm |

TABLE 17

| Formulation Number | Component | % active in Concentrate | 1:64 Dilution |
|---|---|---|---|
| 17 (4013-15) | Hydrogen Peroxide | 7.5% | 1172 ppm |
| | BTC 885 | 6.4% | 1000 ppm |
| | AMMONYX SO | 0.3% | 47 ppm |
| | Phosphoric Acid | 0.225% | 35 ppm |

TABLE 18

| Formulation Number | Component | % active in Concentrate | 1:64 Dilution |
|---|---|---|---|
| 18 (4013-17) | Hydrogen Peroxide | 7.5% | 1172 ppm |
| | BTC 885 | 6.4% | 1000 ppm |
| | AMMONYX CO | 0.3% | 47 ppm |
| | Phosphoric Acid | 0.225% | 35 ppm |

Results of Use Dilution test for *Pseudomonas aeruginosa* and *Staphylococcus Aureus*.

TABLE 19*

| Formulation Number | 5 min UDT *Pseudomonas* | 5 min UDT *Staphylococcus* |
|---|---|---|
| 1 (3480-47) | 1/60 PASS | 0/60 PASS |
| 2 (prior art) | FAIL | FAIL |
| 3 (3509-02) | 1/60 PASS | 0/60 PASS |
| 4 (3509-01) | 1/60 PASS | 1/60 PASS |
| 5 (3491-100) | 2/60 FAIL | 1/60 PASS |
| 6 (3509-77) | 4/60 FAIL | 3/60 FAIL |
| 7 (3491-19) | 1/60 PASS | 2/60 FAIL |
| 8 (3480-88) | FAIL | FAIL |
| 9 (3491-93) | FAIL | FAIL |
| 10 (3533-24) | FAIL | FAIL |
| 11 (3491-29) | FAIL | FAIL |
| 12 (3491-19) | FAIL | FAIL |
| 13 (3491-06) | FAIL | FAIL |
| 14 (3491-68) | FAIL | FAIL |
| 15 (3491-56) | FAIL | FAIL |
| 16 (3491-91) | FAIL | FAIL |
| 17 (3509-48) | FAIL | FAIL |
| 18 (4013-15) | 0/60 PASS | 0/60 PASS |
| 19 (4013-17) | 0/60 PASS | 0/60 PASS |

*Note:
Pass/Fail conclusion based on present day EPA UDT criteria of 0 or 1 sample out of 60 samples showing growth for a pass. It is contemplated that some of these formulations denominated as fail under current EPA standards may actually pass if new regulations are adopted.

The components of the formulation tested under the OECD criteria can be found in Table 20 below. The results of the OECD test for key target organisms such as *Pseudomonas aeruginosa* and *Staphylococcus aureus* can be found in Table 21.

TABLE 20

| Formulation Number | Component | % active in Concentrate | 1:64 Dilution |
|---|---|---|---|
| 20 (3985-31) | Hydrogen Peroxide | 7.5% | 1172 ppm |
| | BTC 885 | 6.4% | 1250 ppm |
| | AMMONYX LO | 0.3% | 47 ppm |
| | Phosphoric Acid | 0.225% | 35 ppm |

Results of OECD test for *Pseudomonas aeruginosa* and *Staphylococcus Aureus*.

TABLE 21

| Formulation Number | 5 min OECD *Pseudomonas* | 5 min OECD *Staphylococcus* |
|---|---|---|
| 20 (3985-31) | ≥6 $\log_{10}$ | ≥4 $\log_{10}$ |

Example 3

Critical Micelle Concentrations

The compositions tested using the use dilution test were tested for their critical micelle concentration by determining the surface tension using a tensiometer. Briefly, a platinum rectangular plate is dipped into a solution of increasing concentration of the measured substance and the surface tension is measured using the tensiometer. The surface tension vs. concentration is plotted and it is the point in the curve that the surface tension does not change that is the critical micelle concentration of that particular mixture. The results can be found in Table 22.

TABLE 22

| Formulation Number | Pass/Fail 5 min UDT Test | Critical Micelle Concentration (CMC) |
|---|---|---|
| 4 (3509-01) | Pass | 373 ppm quat |
| 6 (3509-77) | Fail | 235 ppm quat |
| 10 (3353-24) | Fail | 152 ppm quat |
| 11 (3491-29) | Fail | 150 ppm quat |
| 9 (3491-93) | Fail | 207 ppm quat |
| 12 (3491-19) | Fail | 225 ppm quat |

Example 4

Germicidal Spray Test

Compositions of the present technology are tested using the germicidal spray test at an end use concentration of a concentrated form (no dilution), a 1:10 dilution, a 1:32 dilution and a 1:64 dilution.

AOAC Germicidal Spray Products Testing of Aerosol Detergent/Disinfectant can be found in the Official Methods of Analysis of the AOAC (international Seventeenth Edition), 2002, Chapter 6, Section 6.3.04 entitled "Germicidal Spray Products as Disinfectants." This method is similar to the Use Dilution method. Briefly, for example, *Staphylococcus aureus*, *Salmonella enterica*, and *Pseudomonas aeruginosa* can be used as the test microbe inoculum for efficacy claims. Culture suspensions of each test microbe will be mixed with 5% sterile horse serum (used as the soil load). Cleaned 18×36×2 mm glass slides will be rinsed in isopropyl alcohol and deionized water and placed individually in glass Petri dishes and autoclaved at 121-124° C. for no less than 20 minutes and stored at 36±1° C. prior to the test. 0.01 ml of each of the test microbes containing 5% horse serum are pipetted onto the glass slides. The inoculum will be spread over the entire surface of the slide using a flamed and cooled nichrome wire hood. The slides are placed in a 36±1° C. incubator for 30-40 minutes. Testing will be performed against each test microbe by spraying 10 inoculated dried glass slide carriers at 20±2 second intervals with the test substance (composition). Spraying will be at a distance of 6-8 inches from the inoculated surface of the glass slide carrier for 3-5 minutes or until completely wetted. This process will be continued, timed, and recorded in the raw data sheet. At the end of each contact period, each treated glass slide carrier will be transferred again, at 20±2 second intervals to one 20 ml test tube of Lysogeny broth (LB) per glass slide carrier (primary subculture). These tubes are subcultured at 36±1° C. for 48 hours and observed for the absence or presence of visible growth (turbidity). The absence of visible growth in the primary subculture tube indicates adequate disinfectant activity of the test substance.

Example 5

Cleaning Properties

The cleaning properties of compositions of the present technology may be tested using the Gardener Straight Line Scrubber Test. This method is described in ASTM D4488-95, "Standard Guide for Testing Cleaning Performance of Products Intended for Use on Resilient Flooring and Washable Walls", ASTM International, 2001, p. 1-15, incorporated by reference in its entirety. The composition of the present technology is evaluated by Section A5 of ASTM D4488-95 for % soil removal to determine the cleaning effectiveness of the formulations, and tested by a filming and streaking method to determine effectiveness as a hard surface cleaner. The formulation is diluted 1:64 with deionized water before performing the test. Briefly, the A5 test is the following:

(1) Prepare a particulate soil by adding in the order listed: 38% weight natural humus, 1% weight paraffin oil, 1.5% weight used crankcase motor oil, 17.7% weight Portland cement, 18% weight silica, 1.5% weight carbon, lampblack, 0.3% weight iron oxide, 18% weight Bandy black clay, 2.0% weight stearic acid, and 2% weight oleic acid. The soil is mixed by hand in a glass beaker and transferred to a ball mill. Measure out one and one-half times its volume of water in the empty beaker. Swirl water around vigorously several times to suspend any of the soil mixture that may be adhering to the sides of the beaker. Add water to the mill. Mix for 18 h and when completely dry, pulverize using a mortar and pestle and screen through 300 mesh screen.

(2) Prepare an oily blend over a steam bath: 12 parts kerosene, 12 parts Stoddard solvent, 1 part paraffin oil, 1 part SAE 10 motor oil, 1 part vegetable shortening, 3 parts olive oil, 3 parts linoleic acid, 3 parts squalene, 3 parts 1-octadecene. Mix all-vegetable shortening in appropriate sized glass beaker over steam bath. Then add paraffin oil, SAE 10 motor oil, and olive oil. Cover beaker and blend in remaining ingredients. Continue to mix until uniform, straw-colored liquid is obtained.

(3) Cover vinyl tile with brass template. Place 50 mg (0.05 g) of particulate soil into the center area. Wet a double thickness paper toweling (1¼ by 2½ inch) with 5 drops of the oily blend. Set the paper towel over the soil mound and leave in place for about 10 seconds. Begin rubbing the soil into the tile using a circular motion and moderate pressure. Continue application until the framed area is evenly soiled.

(4) Allow soiled tiles to air dry for 24 hours before cleaning.

(5) After proper calibration of the tristimulus colorimeter, set its data processor to L, a, b, mode. Read reflectance of vinyl tiles before and after soiling by taking 3 readings per tile.

(6) Cleaning: Place the soiled tile on the washability apparatus using additional pieces of tile to hold the soiled panel in place. Wet the panel, in the center of the soiled area with 20 ml of the test solution and allow to stand for 1 minute. After approximately 30 s has elapsed, pour an additional 50 ml of the test solution onto the wrung-out wet sponge in the sponge holder. When 1 minute is up, invert the sponge so that the wet side is in contact with the soiled tile. Scrub for 10 cycles. Remove panel and rinse with tap water.

(7) Read the reflectance of the cleaned tiles (3 readings per tile) and use the mean of the three readings to calculate % cleaning efficiency: % cleaning efficiency=(R1−R2)/(R3−R2).

A method for filming and streaking assay is as follows:

(1) Black tiles or mirrored tiles are cleaned with a standard spray and wipe glass cleaner. The tiles are then rinsed with isopropyl alcohol and allowed to dry.

(2) Ten drops of hard surface cleaner sample is evenly applied around the hard surface material. The drops should be applied in a uniform pattern, size and shape on the hard tile surface.

(3) The treated tile is wiped with a quartered tissue which has been folded in half. The tissue is wiped across the tiles' surface for ten cycles while applying light and uniform pressure. One cycle is equal to one back and forth motion.

(4) The hard surfaces are dried for a minimum of 10 minutes.

(5) The hard surfaces are then visually evaluated and scored under well lighted conditions. The scoring of the streaking and filming performance is conducted using a plus or minus rating scale, where the control is set to zero and a positive score is indicative of superior performance.

The present technology is now described in such full, clear and concise terms as to enable a person skilled in the art to which it pertains, to practice the same. It is to be understood that the foregoing describes preferred embodiments of the present technology and that modifications may be made therein without departing from the spirit or scope of the present technology as set forth in the appended claims. Further the examples are provided to not be exhaustive but illustrative of several embodiments that fall within the scope of the claims.

The invention claimed is:

1. A composition comprising:
about 7.5% hydrogen peroxide by weight,
about 6.4% of a quaternary ammonium compound by weight;
about 0.3% amine oxide by weight;
about 0.225% phosphoric acid by weight; and
water,
wherein the quaternary ammonium compound comprises n-alkyl dimethyl benzyl ammonium chloride wherein n-alkyl is 50% C14, 40% C12, 10% C16, n-octyl decyl dimethyl ammonium chloride, di-n-octyl dimethyl ammonium chloride, and di-n-decyl dimethyl ammonium chloride.

2. The composition of claim 1, wherein the amine oxide is selected from the group consisting of lauramine oxide, stearamine oxide and cetamide oxide.

3. The composition of claim 1, wherein the composition is a dilutable composition diluted in a diluent.

4. The composition of claim 3, wherein the dilutable composition is diluted at a ratio of 1:10, 1:32, or 1:64.

5. The composition of claim 3, wherein the diluted composition has a pH of about 6.0 to about 8.0.

6. The composition of claim 1, wherein the composition has a pH of about 4 or less.

7. A dilutable biocidal composition comprising:
about 7% to about 7.5% by weight hydrogen peroxide;
about 6% to about 6.8% by weight quaternary ammonium compound;

about 0.25% to about 0.35% by weight amine oxide;
about 0.2% to about 0.4% by weight stabilizer; and
water
wherein the dilutable biocidal composition, when diluted, provides a microbial contact kill time of less than about 5 minutes for at least one biocidal target, and
wherein the quaternary ammonium compound comprises n-alkyl dimethyl benzyl ammonium chloride wherein n-alkyl is 50% C14, 40% C12, 10% C16, n-octyl decyl dimethyl ammonium chloride, di-n-octyl dimethyl ammonium chloride, and di-n-decyl dimethyl ammonium chloride.

8. The dilutable biocidal composition of claim 7, wherein the composition comprises:
about 7.4% to about 7.6% by weight hydrogen peroxide;
about 6.2% to about 6.6% by weight quaternary ammonium compound;
about 0.28% to about 0.32% by weight amine oxide; and
about 0.22% to about 0.24% by weight phosphoric acid as the stabilizer.

9. The dilutable biocidal composition of claim 7, wherein the composition comprises:
about 7.5% by weight hydrogen peroxide,
about 6.4% by weight quaternary ammonium compound,
about 0.3% by weight amine oxide, and
about 0.225% by weight phosphoric acid as the stabilizer.

10. The dilutable biocidal composition of claim 7, wherein the dilutable composition is diluted at a ratio of 1:10, 1:32 or 1:64 in a diluent.

11. The dilutable biocidal composition of claim 7, wherein the dilutable biocidal composition has a critical micelle concentration at the end use dilution of about 300 ppm to about 400 ppm.

12. The dilutable biocidal composition of claim 7, wherein the pH of the composition is about 6.0 to about 8.0.

13. The dilutable biocidal composition of claim 7, wherein the biocidal target is at least one bacterium, at least one virus, at least one protozoa, at least one spore, at least one fungus, or combinations thereof.

14. The dilutable biocidal composition of claim 13, wherein the at least one bacterium comprises a gram negative or a gram positive bacteria, wherein the at least one bacterium is a member selected from the group consisting of *Campylobacter jejuni, Pseudomonas aeruginosa, Salmonella enterica, Staphylococcus aureus, Streptococcus pyogenes*, and *Clostridium difficile*.

15. The dilutable biocidal composition of claim 13, wherein the at least one bacterium comprises *Staphylococcus aureus*.

16. The dilutable biocidal composition of claim 13, wherein the at least one bacterium comprises *Pseudomonas aeruginosa*.

17. The dilutable biocidal composition of claim 13, wherein the at least one bacterium comprises *Salmonella enterica*.

18. The dilutable biocidal composition of claim 13, wherein the at least one bacterium comprises *Salmonella enterica, Pseudomonas aeruginosa*, and *Staphylococcus aureus*.

19. The dilutable biocidal composition of claim 13, wherein the at least one fungus comprises *Candida albicans* or *Aspergillus niger*.

20. The dilutable biocidal composition of claim 7, wherein the amine oxide is selected from the group consisting of lauramine oxide, octyl amine oxide, decyl amine oxide, stearamine oxide, cetamide oxide, myristamine oxide, lauramidopropylamine oxide, and tetradecyl amine oxide.

21. A method of cleaning a hard surface comprising:
providing a composition comprising
about 1172 ppm hydrogen peroxide,
about 1000 ppm quaternary ammonium compound,
about 47 ppm amine oxide,
about 35 ppm phosphoric acid, and
water;
contacting at least one soiled surface or substrate with the composition; and
removing the composition or soil from the surface or substrate.

* * * * *